United States Patent [19]
Perrotta et al.

[11] Patent Number: 5,800,597
[45] Date of Patent: Sep. 1, 1998

[54] INTEGRAL COALESCER FILTER-MEMBRANE DEVICE TO PROVIDE A FILTERED GAS STREAM AND SYSTEM EMPLOYING SUCH DEVICE

[75] Inventors: Kenneth A. Perrotta, Salem, N.H.; Dean Hoyt, Burlington, Mass.

[73] Assignee: Whatman Inc., Haverhill, Mass.

[21] Appl. No.: 786,808

[22] Filed: Jan. 21, 1997

Related U.S. Application Data

[60] Provisional application No. 60/015,192, Apr. 12, 1996.
[51] Int. Cl.$^6$ ............................................. B01D 53/22
[52] U.S. Cl. ............................ 96/9; 96/11; 96/179; 96/180; 55/270; 55/318; 55/333; 55/340; 55/487
[58] Field of Search .................... 55/318, 320, 327, 55/330, 332, 333, 340, 421, 486, 487, 502, 527; 95/45, 273, 286, 287; 96/4, 7, 9, 11, 179, 180

[56] References Cited

U.S. PATENT DOCUMENTS

| | | | |
|---|---|---|---|
| 3,455,792 | 7/1969 | Ohta | 95/273 X |
| 3,802,160 | 4/1974 | Foltz | 95/273 |
| 3,926,561 | 12/1975 | Lucero | 95/45 X |
| 4,102,785 | 7/1978 | Head et al. | 55/487 X |
| 4,572,724 | 2/1986 | Rosenberg et al. | 96/179 X |
| 4,886,528 | 12/1989 | Aaltonen et al. | 96/7 X |
| 4,932,987 | 6/1990 | Molina | 55/487 X |
| 4,941,900 | 7/1990 | Cordes | 55/333 X |
| 5,368,021 | 11/1994 | Beard et al. | 96/4 X |

Primary Examiner—Robert Spitzer
Attorney, Agent, or Firm—Richard P. Crowley

[57] ABSTRACT

An integral coalescer filter-membrane device to provide clean sample gas to gas analyzers. The device includes a housing, an inlet port for feed gas, an outlet port to withdraw clean sample gas essentially free of entrained liquids, such as water, and particulate material which might contaminate or interfere with the gas analyzer, a bypass port and a drain port to remove by gravity coalesced liquid. The device includes a filter tube to coalesce and filter the feed gas stream and a chamber having a supported hydrophobic selected porosity membrane. The outlet port receives clean sample gas from the upper portions of the chamber, while the bypass port removes coalesced filtered gas from a lower chamber.

15 Claims, 3 Drawing Sheets

INTEGRAL COALESCER FILTER-MEMBRANE DEVICE TO PROVIDE A FILTERED GAS STREAM AND SYSTEM EMPLOYING SUCH DEVICE

This application claims the priority U.S. Ser. No. 60/015, 192, filed Apr. 12, 1996, incorporated herein by reference.

REFERENCE TO PRIOR APPLICATION

Applicants claim the priority date of U.S. provisional patent application Ser. No. 60/015,192, filed Apr. 12, 1996, hereby incorporated by reference in this application.

BACKGROUND OF THE INVENTION

Gas streams containing particulate matter and entrained liquid are often required to be sampled for a wide variety of applications and uses. Typically, the removed feed or gas sample must be treated to remove particulate matter and also entrained liquid to prevent damage or contamination to the gas analyzer or gas sample system components.

Generally, gas samples may be taken from a variety of gas streams; such as, but not limited to: stack exhaust streams; automotive exhaust streams; natural and synthetic gas streams; landfill or waste gas streams; hydrocarbon streams; chemical gas process streams; nitrogen; helium; argon, and/or oxygen gas streams; and/or oxides of nitrogen and sulfur gas streams.

Such gas streams often contain fine particulate matter, like soot and chemical particles, and entrained liquid, particularly water, which may interfere in the efficient and accurate operation of any downstream gas stream analyzer. Typical analyzers useful with gas samples include gas analyzers, like gas chromatographs, mass spectrometers, emission analyzers, or other gas instruments to measure volume, pressure, temperature, composition, and concentration of gas, and mixtures thereof.

It is desirable to provide new and improved compact, integral and efficient gas sample devices to provide gas samples for instruments, and to provide systems employing such gas devices.

SUMMARY OF THE INVENTION

The invention relates to an integral, compact coalescer filter-membrane device for sample gas streams for use with gas analyzers and other clean gas-user devices.

The invention comprises an integral coalescer filter-membrane device for sample gas filtration applications. The device provides for prefiltration of a sample gas stream, typically containing liquid particles and particulate material, to remove the particulate matter, resulting in extended life of the membrane employed in the device. The device also includes prefiltration of all liquid aerosols by the hydrophobic coalescer filter-membrane in the device, resulting in an extended membrane life; that is, chemical attack of the membrane by aerosols found in the process stream is minimized as a result of coalescing and draining of liquid from the feed gas stream. The device further provides for removal of entrained liquid from the feed gas stream. The device also provides for enhanced liquid separation capabilities from the feed or sample gas stream, of interest due to the orientation of the integral coalescer device in a generally vertical configuration by gravitational effect on the coalesced liquid, e.g. water, from the feed-sample gas stream. Additionally, a liquid sump in the device provides for an additional reservoir for coalesced liquids.

The device of the invention provides both continuous coalescing of all liquid and the security of a hydrophobic membrane in a simple, integral compact device. The device requires fewer fittings in use than separate filters and membranes, thereby reducing the risk of leaks. The device is compact and requires less maintenance and downtime, as the supported replaceable coalescer membrane is fully protected from solids and liquids removed by the filter. The device is employed upstream of the sample gas apparatus, such as an analyzer. There is no need for separate prefiltration of the sample gas, which would place more volume in the sample system, more space for installation and potential for more leaks.

The device includes a housing which contains a porous membrane filter which is supported on and by a sintered porous disc located on the outlet side of the housing. In operation of the device, the gas sample enters the device through an inlet port and is directed downwardly inside and through the coalescing-particulate filter, particularly a filter tube of selected porosity and pressure drop properties. The coalescer filter entraps all the particulate matter to a defined, very low level, and coalesces the entrained liquid droplets; e.g. water, oil, solvents, etc., and continuously drains by gravity the coalesced liquid from the outlet drain. The filtered sample gas, free of entrained liquid particles, then flows upwardly, after passing through the coalescing filter within the housing, to the upstream side of the supported membrane and exits therefrom after passing through the membrane from the outlet part on the downstream side of the membrane as gas only, for use in an analyzer, while a bypass gas stream is removed for return to the feed gas stream through a bypass outlet port on the downstream side of the membrane. The bypass filtered gas stream may be returned to the main process stream, discharged to waste or used for pollution control or other purposes. Any entrained liquid, e.g. water, will not pass through the porous hydrophobic supported membrane and will exit through the lower drain port.

The membrane employed is generally a hydrophobic membrane and of sufficient porosity to allow the easy flow of gas or vapor therethrough; however, the smaller liquid molecules remain trapped and are unable to flow through the membrane under normal operating conditions. This is due to the high surface tension, which causes liquid, e.g. water, molecules to bond together, which forms molecular groups too large to fit through the membrane pores. The membrane is selected to be inert, flexible, strong, durable and replaceable, and selected for systems designed for ppb, ppm and low percent level concentrations.

The membrane may be selected from a variety of materials and pore sizes and of different thicknesses, e.g. 2–20 mils, but generally and preferably comprises a fluorocarbon membrane material like Teflon® (a trademark of I. E. duPont Co., Inc.), which is hydrophobic for removing water, and generally has a selected porosity of, for example, not greater than about 1.0 microns, like 0.2 or 0.02 microns or less, which is sufficient to block the desired liquid.

The membrane is supported by a porous disc, typically a ceramic or stainless steel or other metal disc of greater porosity than the membrane, such as 5–10 microns or more.

The coalescing filter comprises a single or multiple layer filter in a filter housing, usually comprised of selected bonded glass fibers to provide the desired filtration, such as a resin (silicon or fluorocarbon) bonded borosilicate glass fiber tube, which may include additional foam or fiber, such as a bonded glass fiber layer, for coalescing purposes. The ends of the filter tube often are selected to be compressed to form an end seal against the plate without the need for separate end gaskets. For example, suitable filter tubes would have a rating of 99.99% at 0.1 microns to 93% at 0.1 microns and include various grades, e.g. Grade "X", of bonded Balston® filter tubes from Whatman, Inc., of Haverhill, Mass.

The invention will be described for the purposes of illustration only in the following embodiments; however, it should be recognized that various additions, modifications, and changes may be made to the described embodiments by those persons skilled in the art without departing from the spirit and scope of the invention.

DESCRIPTION OF THE EMBODIMENTS

Figure 1:
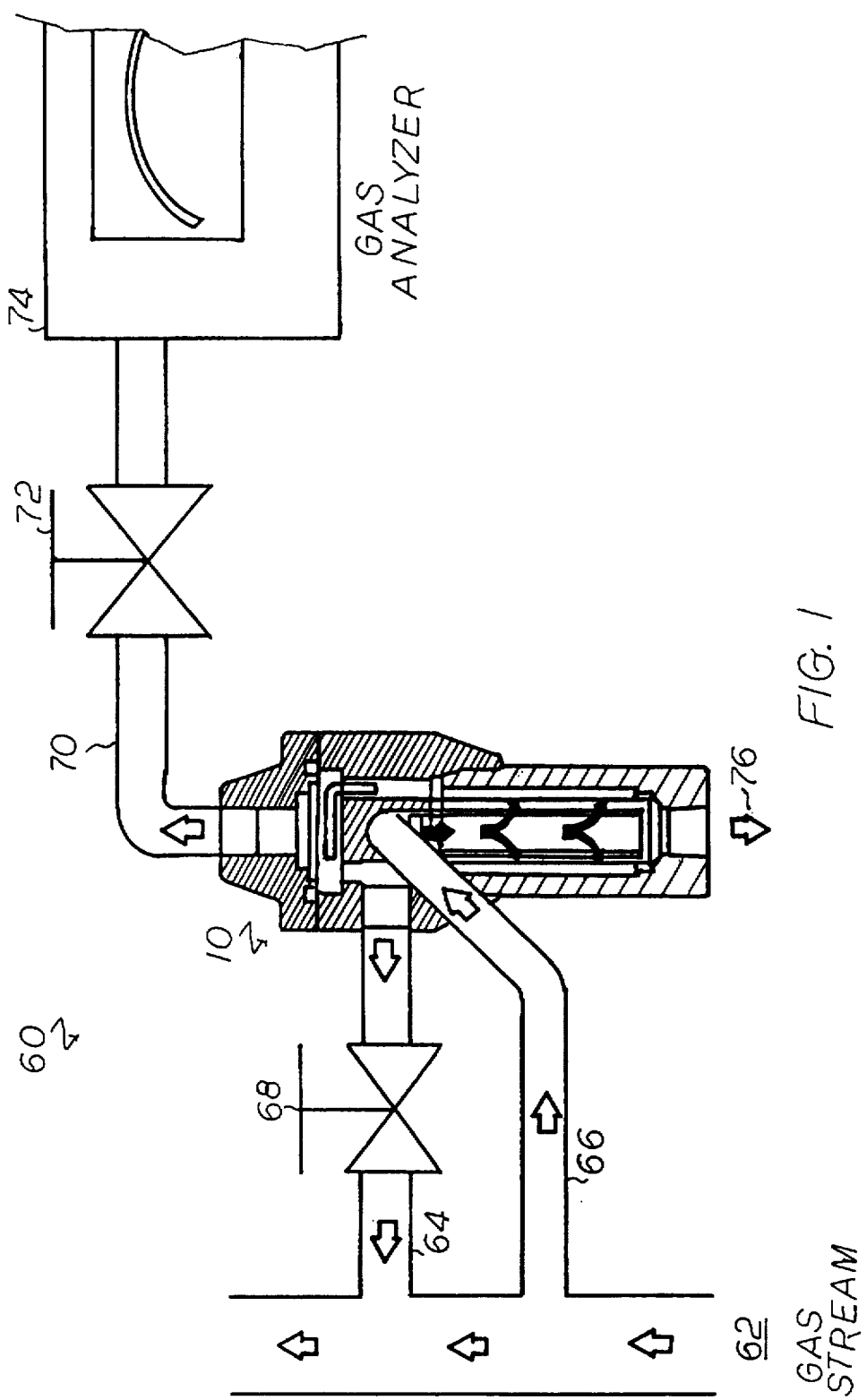
FIG. 1 is a schematic illustration of a gas sample system employing the integral filter-membrane device of the invention.

As illustrated in the drawings, the component parts of the integral coalescer filter-membrane device of the invention are as follows:

10 integral coalescer filter-membrane device
12 head element
14 sample gas conduit
16 membrane chamber
18 hydrophobic membrane; e.g., fluorocarbon 0.1–10 microns porosity
20 O-rings
22 base element
24 inlet for gas feed stream
26 base membrane chamber
28 filtered gas passageway
30 side outlet for bypass gas stream
32 threaded opening to receive filter housing
34 filter housing
36 drain opening
38 filter tube—resin bonded glass fiber
40 coalescer layer—coarse glass fiber for coalescing and liquid drainage over 90% at 0.1 microns
42 peripheral chamber about filter
44 seals
46 threads
48 filter tube sealing surface plate
50 membrane porous sintered membrane backup or support plate
52 sump
60 analyzer system
62 process gas stream
64 bypass gas stream
66 gas stream conduit
68 recycle flow control valve
70 sample gas
72 sample flow control valve
74 gas analyzer
76 liquid drain The invention comprises an integral coalescer filter-membrane device 10 for the filtering of a liquid-particulate containing a gas sample stream, such as an oxygen, nitrogen, or hydrocarbon feed stream, to attain a filtered liquid and gas bypass stream, and a sample gas stream; for example, for use in a gas analyzer. The device comprises a head element 12 having a sample gas conduit 14 having a one and an other end extending therethrough, the one end comprising a sample gas outlet for the retrieval of a sample gas stream therefrom, a head bottom membrane chamber 16 with an O-ring 20 between head element 12 and base element 22, a membrane 18 extending across the membrane chamber, and an other end on the opposite side of the membrane. The membrane is supported by a ceramic or stainless steel, or other metal, disc membrane support plate 50 of greater porosity than the membrane, and generally of sintered material. The device also includes a base element 22 secured to the head element 12 with O-ring seals 20 having an inlet 24 for the introduction of the gas feed stream and a side outlet 30 for the withdrawal of the bypass gas stream. Typically, the inlet and outlets are placed on the side, and generally on the same plane, within a base top membrane passage adjacent and opposite the head bottom membrane chamber 16, across the hydrophobic membrane surface 18 to permit the transverse flow of a filtered feed gas stream across the filtered gas passageway 28 on the base element 22 having a bottom opening.

The device also includes a filter device having a top and bottom, the filter device comprised of an elongated, vertically disposed filter housing 34 threadably secured in an opening 32 in the base element 22, having a top and bottom, and vertically secured within the bottom opening of the base element 22, and having a filter tube 38 therein within the filter housing 34 and spaced apart therefrom, the filter tube 38 designed to provide for the filtration of the feed gas stream with the ends compression sealed in the housing 34; and, typically, would comprise a replaceable resin-bonded, glass fiber microglass filter tube having an outer periphery porous glass fiber or foam drain layer 40 thereabout, the filter tube spaced apart from the housing to form a peripheral chamber 42 about the filter tube, and coalescer layer 40 to receive a filtered gas stream from the filter tube 38, and which peripheral chamber 42 is in fluid flow communication with the base top membrane chamber 26 through filtered gas passageway 28, which membrane chamber 26 is in fluid flow communication with the bypass outlet 30, thereby to permit the transverse flow of a filtered gas feed stream across the surface of the hydrophobic membrane 18.

The filter tube 38 has a first open end, and is in fluid flow communication with the gas feed stream inlet 24 to receive the feed stream within the interior of the filter tube 38. The filter housing 34 has a lower drain opening 36 for the discharge of coalesced liquid from the feed gas stream from the coalescer layer 40 of the filter tube 38, whereby a gas stream introduced into the unit is passed through the interior of the filter tube 38, is filtered, passes through the peripheral chamber 42 about the filter tube 38 through the filtered gas passageway 28 and into the base membrane chamber 26, and a bypass gas stream is withdrawn from the bypass outlet 30 and the filtered gas stream passes through the hydrophbic membrane 18 into the head bottom membrane passageway and is discharged through the sample gas outlet as a filtered gas stream. A liquid sump 52 in the device provides for an additional reservoir for coalesced liquids.

Generally, the gas feed stream inlet 24 and the gas bypass outlet 30 are disposed at an angle of about, or at least, about ninety degrees from each other. Also, generally, the filter housing 34 is removably and threadably secured by threads 46 and seals 44 in the bottom opening of the base element 22, to permit easy replacement of the filter tube 38 and coalescer layer 40. The filtered bypass gas stream may be recycled to the feed stream or passed to waste or exhaust, or passed to another type of device, such as a pollution control device, or otherwise disposed of. A filtered sample gas stream, typically free of particulate matter and aerosol particles, is removed for use, particularly as a gas analyzer, such as a process gas analyzer, to determine the composition and concentration of the gas components.

FIG. 1 shows a schematic representation of the integral coalescer filter-membrane device of the invention 10 within an analyzer system 60. The process gas stream 62 is diverted through inlet gas stream conduit 66 to the filter-membrane device 10. The gas stream then passes through the filter-membrane device and the entrained liquid drains out of the liquid drain 76. The bypass gas stream 64 is controlled by a flow control valve 68, and the sample gas 70 passes up out of the device 10 to a gas analyzer 74. This process is controlled by flow control valve 72.

Figure 2:
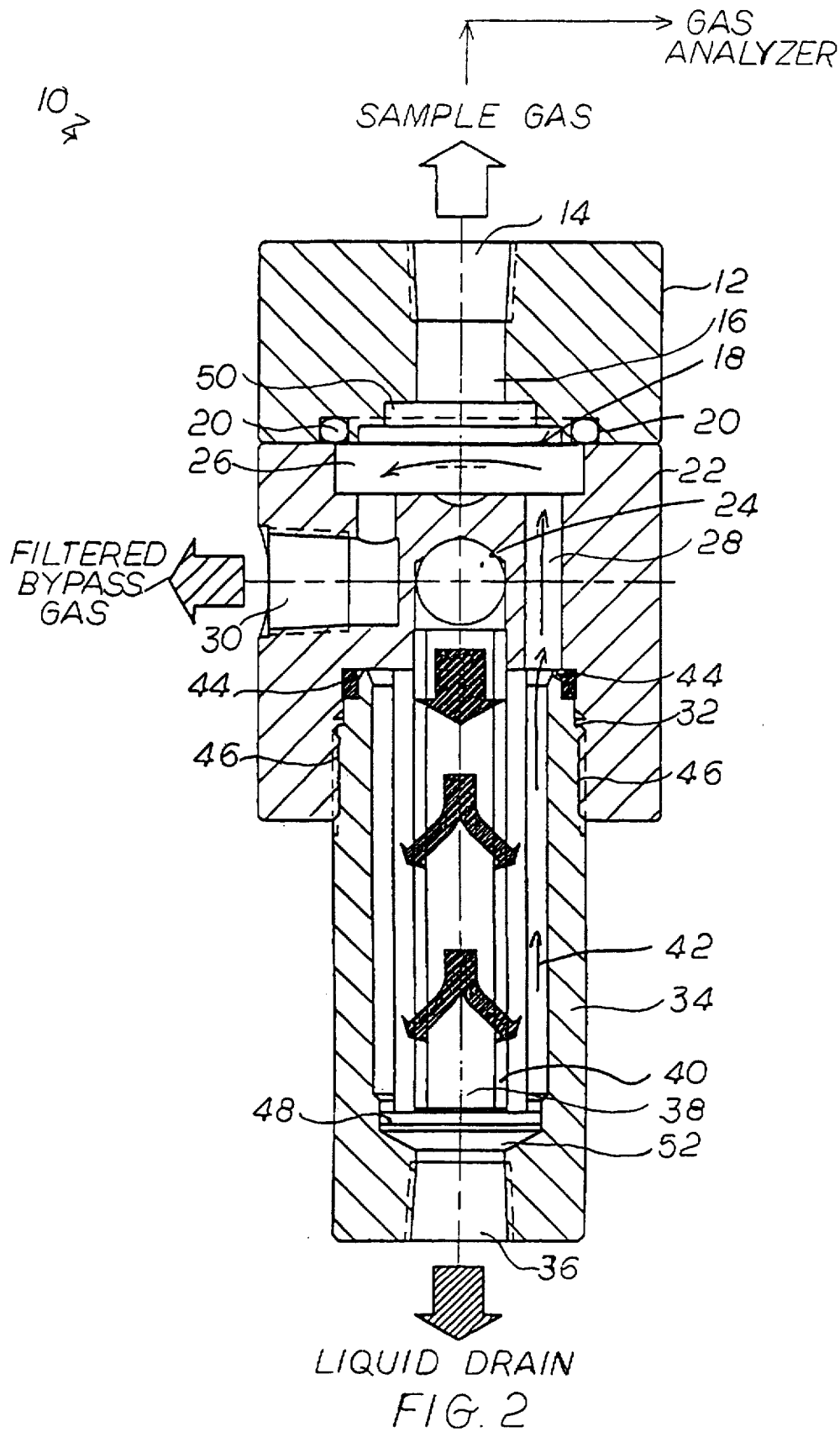
FIG. 2 is a schematic, cross-sectional view of the device of the invention.
Figure 3:
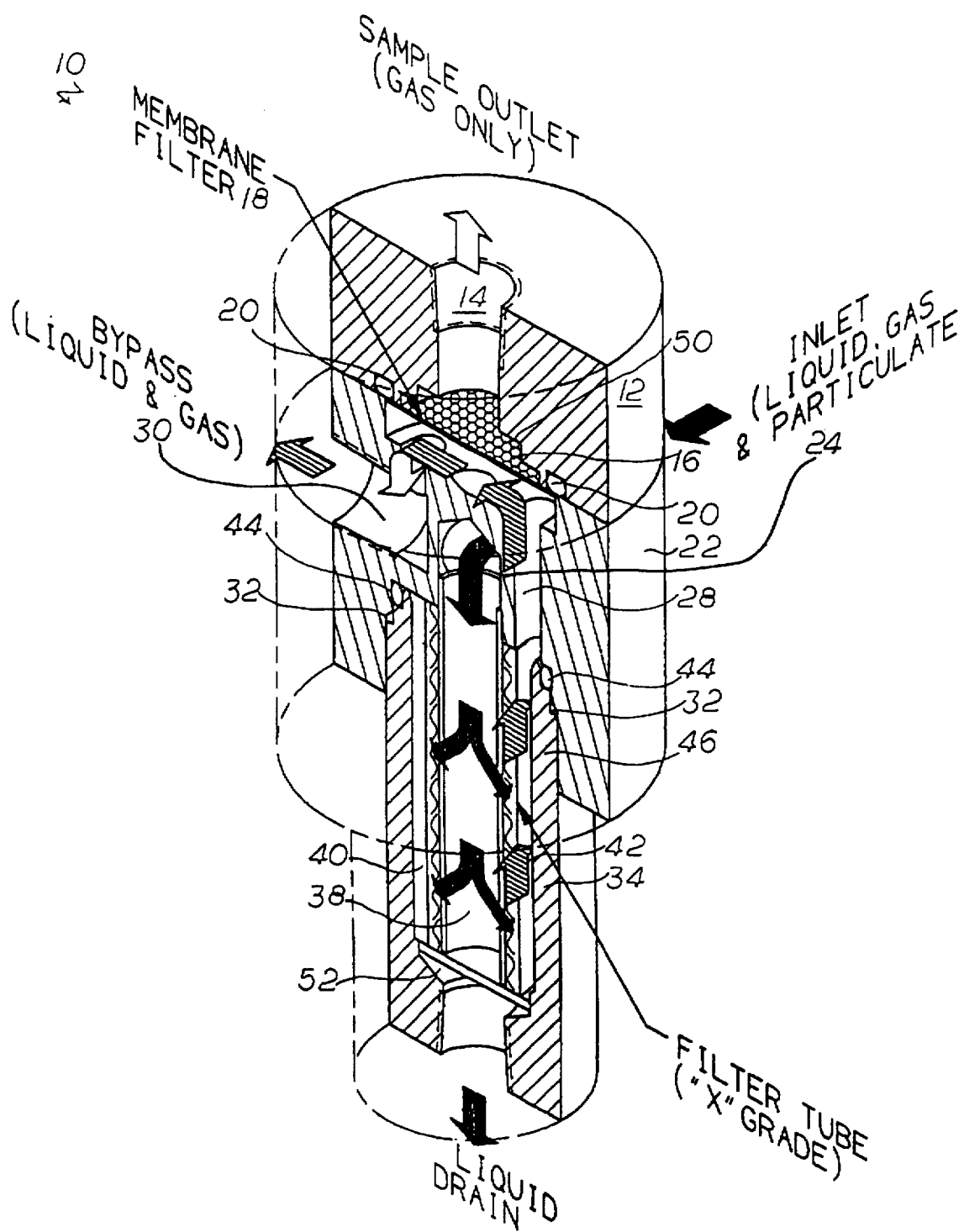
FIG. 3 is a perspective, cutaway sectional view of the device of FIG. 2.

FIGS. 2 and 3 show the filter-membrane device of the invention 10, with FIG. 2 a sectional view and FIG. 3 a perspective sectional view. The drawings illustrate the device 10 with a head element 12 housing the sample gas conduit 14 leading to a head bottom membrane chamber 16 and a hydrophobic membrane 18 extending across the membrane chamber. The device also includes a base element 22 secured to the head element 12 and sealed with O-rings 20 and having an inlet 24 for the introduction of the gas feed stream, and a side outlet 30 for the withdrawal of the bypass gas stream.

Base element 22 is secured to a vertically disposed filter housing 34, vertically secured within the bottom opening of the base element 22, and having a filter tube 38 within the filter housing 34 sealed at ends, and the walls spaced apart therefrom, to form a peripheral chamber 42 about the filter tube and coalescer layer 40 to receive a filtered gas stream from the filter tube 38. The peripheral chamber 42 connects to the base top membrane chamber 26, through filtered gas passageway 28, which membrane chamber 26 connects to the bypass outlet 30, to permit the transverse flow of a filtered gas feed stream across the surface of the hydrophobic membrane 18.

The filter tube 38 is in fluid flow communication with the gas feed stream inlet 24 to receive the feed stream within the interior of the filter tube 38. The housing has a lower drain opening 36 for the discharge of coalesced liquid from the feed gas stream from the coalescer layer 40 of the filter tube 38. Generally, the gas feed stream inlet 24 and the gas bypass outlet 30 are disposed at an angle of about ninety degrees from each other. Also, generally, the filter housing 34 is removably and threadably secured in the bottom opening of the base element 22 to permit easy replacement of the filter tube and coalescer layer 40.

Thus, the device of the invention provides both continuous coalescing of all liquids and the security of a hydrophobic membrane in a simple, integral compact device. The device requires fewer fittings in use than separate filters and membranes, thereby reducing the risk of leaks. The device is compact and requires less maintenance and downtime, as the supported replaceable coalescer membrane is fully protected from solids and liquids removed by the filter.

What is claimed is:

1. An integral coalescing filter-membrane device, adapted for use with a gas feed stream containing entrained liquid and solid particulate material, to provide a clean sample gas essentially free of entrained liquid and particulate material, adapted for use in a gas analyzer, which device comprises:
   a) a housing having a one upper end with a chamber and an other lower end;
   b) an inlet port for the introduction of the feed gas stream;
   c) an outlet port for the withdrawal of a clean sample gas;
   d) a bypass port for the withdrawal of a bypass coalesced-filtered gas stream;
   e) a drain port at the other lower end of the housing for the gravity discharge of a coalesced entrained liquid;
   f) a coalescing filter tube having an interior and an exterior and a first upper end and a second lower end, and with said ends sealed within the housing, said filter tube designed to filter out particulate material and to coalesce the entrained liquid from the gas feed stream introduced from the inlet port at the first upper end and into the interior of the filter tube, and to provide a coalesced filtered gas stream at the exterior of the filter tube and into the chamber, and to provide a coalesced entrained liquid to be discharged from the drain port at the second lower end;
   g) a porous membrane support plate in the chamber to provide an upper chamber in fluid flow communication with the outlet port and a lower chamber in fluid flow communication with the bypass port; and
   h) a porous membrane of selected porosity supported by the support plate to provide for a clean sample gas into the upper chamber and to the outlet port and to provide for the withdrawal of the coalesced, filtered gas stream in the lower chamber through the bypass port.

2. The device of claim 1 wherein the filter tube comprises a resin-bonded, randomly disposed, glass fiber filter tube.

3. The device of claim 1 wherein the filter tube comprises a multilayer filter tube having an inner tubular layer for removing solid particulate material and an outer adjacent tubular layer for coalescing entrained liquid particles for drainage from the outer layer.

4. The device of claim 1 wherein the filter tube is characterized by at least about 90 percent removal of particulate material of 0.1 microns or more.

5. The device of claim 1 wherein the filter tube comprises a multilayer filter tube composed of resin-bonded glass fibers sealable by compression at each end.

6. The device of claim 1 wherein the porous support plate has a porosity of about 5 to 20 microns.

7. The device of claim 1 wherein the membrane comprises an inert hydrophobic membrane having a thickness of about 1 to 20 mils.

8. The device of claim 1 wherein the membrane has a porosity of about 0.1 microns or less.

9. The device of claim 1 wherein the membrane comprises a fluorocarbon membrane.

10. The device of claim 1 which includes a sump adjacent the drain port to receive coalesced entrained liquid from the filter tube.

11. A system to provide a clean sample gas, which system comprises:
   a) a source of a gas feed stream containing entrained liquid water and solid particulate materials;
   b) the device of claim 1 to receive at least a portion of the gas feed stream into the inlet port; and
   c) a gas analyzer means to receive the clean sample gas from said device and to analyze the clean sample gas.

12. The system of claim 11 which includes means to recycle the withdrawn coalesced filtered gas stream to said source.

13. The system of claim 11 wherein said source comprises a feed gas stream selected from the group consisting of: a stack exhaust gas; a vehicular exhaust gas; a chemical process gas; a natural or synthetic hydrocarbon gas; oxygen; nitrogen; hydrogen; helium and argon.

14. An integral coalescing filter-membrane device, adapted for use with a gas feed stream containing entrained liquid and solid particulate material, to provide a clean sample gas essentially free of entrained liquid and particulate material, adapted for use in a gas analyzer, which device comprises:

a) a housing having a one upper end with a chamber and an other lower end;
   b) an inlet port for the introduction of the feed gas stream;
   c) an outlet port for the withdrawal of a clean sample gas;
   d) a bypass port for the withdrawal of a bypass coalesced-filtered gas stream;
   e) a drain port at the other lower end of the housing for the gravity discharge of a coalesced entrained liquid;
   f) a coalescing multilayer filter tube having an inner tubular layer for removing solid particulate material and an outer adjacent tubular layer for coalescing entrained liquid particles for drainage from the outer layer, said tube having an interior and exterior and a first upper end and a second lower end, and with said ends sealed within the housing, said filter tube designed to filter out particulate material, and wherein the filter tube is characterized by at least about 90 percent removal of particulate material of 0.1 microns or more, and to coalesce the entrained liquid from the gas feed stream introduced from the inlet port at the first upper end and into the interior of the filter tube, and to provide a coalesced filtered gas stream at the exterior of the filter tube and into the chamber, and to provide a coalesced entrained liquid to be discharged from the drain port at the second lower end;
   g) a porous membrane support plate in the chamber to provide an upper chamber in fluid flow communication with the outlet port and a lower chamber in fluid flow communication with the bypass port;
   h) a sump adjacent the drain port to receive coalesced entrained liquid from the filter tube; and
   i) a porous membrane of selected porosity supported by the support plate to provide for a clean sample gas into the upper chamber and to the outlet port and to provide for the withdrawal of the coalesced-filtered gas stream in the lower chamber through the bypass port.

15. A system to provide a clean sample gas, which system comprises:

a) a source of a gas feed stream containing entrained liquid water and solid particulate materials;
   b) the device of claim 14 to receive at least a portion of the gas feed stream into the inlet port; and
   c) a gas analyzer means to receive the clean sample gas for said device and to analyze the clean sample gas.

* * * * *